United States Patent [19]
Patton

[11] 3,950,416
[45] *Apr. 13, 1976

[54] SYNTHESIS OF DICYANOFORMAMIDES
[75] Inventor: Tad L. Patton, Baytown, Tex.
[73] Assignee: Exxon Research and Engineering Company, Linden, N.J.
[ * ] Notice: The portion of the term of this patent subsequent to Jan. 25, 1989, has been disclaimed.
[22] Filed: Mar. 25, 1974
[21] Appl. No.: 454,516

Related U.S. Application Data
[63] Continuation of Ser. No. 188,434, Oct. 12, 1971, abandoned, which is a continuation-in-part of Ser. No. 685,288, Nov. 24, 1967, Pat. No. 3,637,843.

[52] U.S. Cl. .......................... 260/545 R; 260/77.5 R
[51] Int. Cl.$^2$ ........................................ C07C 63/00
[58] Field of Search ............................... 260/545 R

[56] References Cited
UNITED STATES PATENTS
3,637,843  1/1972  Patton .............................. 260/545

OTHER PUBLICATIONS
Petersen: Annalen der Chemie, Vol. 562, p. 211 (1949).

*Primary Examiner*—Lewis Gotts
*Assistant Examiner*—Dolph H. Torrence
*Attorney, Agent, or Firm*—David A. Roth

[57] ABSTRACT

Dicyanoformamides having aromatic moieties as novel composition of matter are prepared by the reaction of a diisocyanate having an aromatic moiety with two (2) moles of hydrogen cyanide in the presence of a specially defined, hindered catalyst which will not promote further polymerization.

20 Claims, No Drawings

SYNTHESIS OF DICYANOFORMAMIDES

RELATED APPLICATIONS

This is a continuation of application Ser. No. 188,434, filed Oct. 12, 1971, abandoned, which is a continuation-in-part of Ser. No. 685,288 filed Nov. 24, 1967, U.S. Pat. No. 3,637,843.

BACKGROUND OF THE INVENTION

The present invention is directed to the synthesis of dicyanoformamides having the following structure:

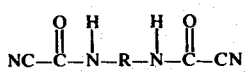

where:
R is the organic moiety of the diisocyanate from which the dicyanoformamide is produced and is aromatic, alkyl substituted aromatic, or functionally substituted derivatives thereof.

It has been disclosed by S. Petersen in *Annalen der Chemie* 562, 205–226 (1949) that a hexamethylene dicyanoformamide is formed by the reaction of hydrogen cyanide with hexamethylene diisocyanate. There is no disclosure, however, of the formation of dicyanoformamides having an aromatic moiety as set forth above. Further, the procedure set forth by S. Peterson in making the aliphatic dicyanoformamides cannot be used to produce a dicyanoformamide having an aromatic moiety.

SUMMARY OF THE INVENTION

New dicyanoformamides having an aromatic moiety are prepared by the reaction of a diisocyanate having an aromatic moiety with two (2) moles of hydrogen cyanide in the presence of an effective catalyst. It has been found that aromatic diisocyanates are much more reactive than aliphatic diisocyanates with hydrogen cyanide, i.e. about a hundredfold more reactive. Thus, to form the hydrogen cyanide adduct or dicyanoformamides of the present invention, it has been found that the reaction procedure which includes the reaction conditions is critical, especially the catalyst used. Hydrogen cyanide adds to a diisocyanate by the following reaction:

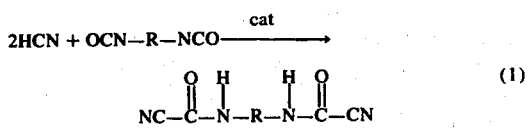

However, another reaction may also occur:

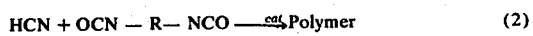

DESCRIPTION OF THE PREFERRED EMBODIMENTS

The dicyanoformamides of the present invention are produced from diisocyanates having the following structure:

where:

R is the organic moiety of the diisocyanate from which the dicyanoformamide is produced and is aromatic, alkyl substituted aromatic and functionally substituted derivative thereof. These moieties will have a molecular weight of about 80 to 10,000, preferably 80 to 3,000, most preferably 80 to 1200.

The organic moieties of the diisocyanates may be substituted with functional groups such as sulfoxy, sulfonyl, alkoxy, aryloxy, ester, alkylthio, arylthio, nitro and the like which do not react with the isocyanate group or with HCN. Functional groups which have active hydrogen atoms (i.e., carboxylic acids, phenols, amines, etc.) should not be present.

Diisocyanates characterized by having aromatic hydrocarbon moieties are exemplified by m-phenylene diisocyanate; p-phenylene diisocyanate; biphenylene diisocyanate; 1,5-naphthalene diisocyanate and the like. The diisocyanates having an alkyl substituted aromatic hydrocarbon moiety are exemplified by toluene diisocyanate; durene diisocyanates; 4,4'-diphenylmethane diisocyanate; 3,3'-dimethyl-4,4'-biphenylene diisocyanate; 4,4'-diphenylisopropylidene diisocyanate and the like. Further, diisocyanates which have the organic moiety functionally substituted may also be used and are exemplified by 4,4'-diphenylsulfone diisocyanate; 4,4'-diphenyl ether diisocyanate; 3,3'-dimethoxy-4,4'-biphenylene diisocyanate and the like.

The formation of the dicyanoformamide involves the addition of two (2) moles of hydrogen cyanide to each mole of diisocyanate. A slight excess of the required quantity of HCN is preferably used in the reaction. As illustrated by reaction (1) above, a catalyst is required. However, the choice of catalysts is critical so that only reaction (1) is promoted. It has been found that a catalyst such as pyridine will promote both reaction (1) and (2) above when the organic moiety of the diisocyanate is aromatic.

The crux of the synthesis is the discovery of the criticality of the particular catalyst used. Thus, a special, narrowly defined catalyst is used, which must satisfy certain boundary criteria.

These are: One does not want to drive the initial reaction to completion, i.e. polymer would result. One does not want to have a catalyst of such innocuousness that there would only be a very slow reaction. One must also keep in mind the difference in reactivity between the aliphatic isocyanates and the aromatic isocyanates. The aromatic isocyanates are about ten to a hundredfold more active than the aliphatic ones. Thus the danger and the possibility of driving the reaction of hydrogen cyanide with an aromatic diisocyanate to completion as a polymer is much greater than when one is dealing with aliphatic diisocyanates.

The specific unique, highly preferred catalysts of the invention are generally rather ineffective with aliphatic isocyanates since they do not have the requisite threshold potential to be activated by the catalysts of the invention.

The catalyst of the invention must generally comply with the following criteria in order to effectively operate according to the thrust of this invention. The necessary characteristics are:

a. it cannot have active hydogens;
b. it must be a basic compound;
c. the basicity is defined as being no greater than $K_b$ of $1 \times 10^{-8}$ and preferably no greater than $K_b$ of $1 \times 10^{-10}$; and d. the catalytic activity must be insufficient to form polymers at normal reaction temperatures.

Particularly preferred subgenus of compounds which will satisfy these criteria are:

1. 2,6-dialkylpyridines having the following formula:

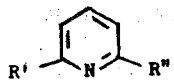

and N,N-dialkylanilines having the following formula:

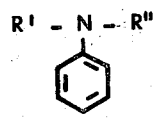

wherein the foregoing schematic formula R' and R'' are $C_1$–$C_{15}$, preferably for the pyridine $C_3$–$C_{10}$, and most preferably $C_3$–$C_6$, and for the aniline preferably $C_2$–$C_{10}$, preferably $C_2$–$C_6$ aliphatic groups. Both R' and R'' can be the same or different within the limitations described above. Furthermore, either R' or R'' can be cyclohexyl.

It is to be noted that 2,6-lutidine, N,N-dimethylaniline, 2,6-diethylpyridine are also specially preferred species but are described and claimed in the parent applicaton.

Additional preferred species which are preferred for the particular embodiment of the invention disclosed herein are N,N-diethylaniline, N,N-dipropylaniline, N-methyl-N-propylaniline, N-cyclohexyl-N-methylaniline, 2,6-dipropylpyridine, 2-ethyl-6-propylpyridine, 2-methyl-6-ethylpyridine and the like.

In both of the above instances the invention contemplates ring-substituted pyridines and anilines so long as in the case of aniline the substituents are only on the 3, 4 and/or 5 positions of the ring. N,N-diethyl-p-toluidine is an example.

It is to be emphasized that these specific hindered catalysts of requisite basicity are to be used in combination with diisocyanates having aromatic moieties. If used with aliphatic diisocyanates, the catalysts are not active enough to generate any reactions within a practical period of time. But since the aromatic diisocyanates are so much more active than the aliphatic ones, the particularly described catalysts of the invention are effective to drive the reaction toward the formation of dicyanoformamides but not so active as to catalyze their reaction with free isocyanate groups.

The reaction of the diisocyanate with hydrogen cyanide is carried out in a suitable solvent so as to better control the reaction. Any conventional solvent can be used as long as it is not reactive with the reactants. Examples of suitable solvents are benzene, toluene, xylene, ethylbenzene, and the like, and mixtures thereof with aliphatic hydrocarbons such as hexane, petroleum ether and the like.

The reaction of a diisocyanate with hydrogen cyanide is exothermic, and further, the polymer forming reaction (2) is promoted by increased temperature. Accordingly, to produce the dicyanoformamides of the present invention, it is necessary to maintain the temperature at less than 25° C. Temperatures of between −10° and 25° C. may be used; however, the reaction solution is maintained preferably between 0° and 15° C.

The dicyanoformamides of the present invention and their preparation are illustrated by the following examples which are set forth for illustration and are not to be considered limiting of the invention.

EXAMPLE 1

A solution of 21 grams (0.75 mole) of hydrogen cyanide and 85 grams of dry toluene and 10 grams of 2,6-lutidine was prepared at ice bath temperatures. To the solution, 62.5 grams (0.25 mole) of 4,4'-diphenylmethane diisocyanate in 135 grams of dry toluene were added dropwise over a period of two hours. While keeping the temperature below 10° C., a solid began to come out of solution. The reaction solution was stirred an additional 30 minutes after completion of the addition. The product (76 grams) was collected on a filter. The product was purified by dissolving it in acetone and filtering the solution into petroleum ether. The pure product melted at 208° C. Analysis calculated for $C_{17}H_{12}N_4O_2$: C, 67.10; H, 3.97; N, 18.41. Found: C, 66.98; H, 4.22; N, 18.20.

The product has a structure as follows:

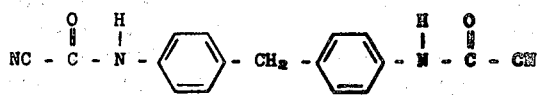

The nuclear magnetic resonance spectrum and the infrared spectrum of the product agreed with the above structure.

EXAMPLE 2

A solution of 34 grams (1.25 moles) of dry hydrogen cyanide, 12 grams of 2,6-lutidine, and 130 grams of toluene was added to a solution of 80 grams (0.32 mole) of 4,4'-diphenylmethane diisocyanate in 300 ml. of dry toluene at 5° C. The solution was allowed to warm slowly to room temperature and an insoluble product was collected on a filter. The infrared spectrum of the product exhibited absorption maxima at 3.05 and 5.90 microns and was identical to the spectrum of the product in Example 1.

The dicyanoformamides of the present invention are useful as monomers in producing a heterocyclic polymer formed by the reaction of the dicyanoformamide with diisocyanates. Further, the dicyanoformamides of the present invention are useful intermediates in reactions with monoisocyanates to form a wide variety of products which are also useful as additives in fuel oils, gasoline, lubricating oils, other polymers and the like. The dicyanoformamides are also useful as curing agents for polyurethanes.

The nature and objects of the present invention having been completely described and illustrated, what I wish to claim as new and useful and secure by Letters Patent is:

1. A process for producing an aromatic dicyanoformamide having the formula:

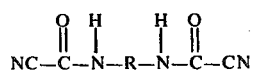

wherein R is an aromatic hydrocarbon free of functional groups containing active hydrogen which comprises:

reacting hydrogen cyanide with a diisocyanate having the same aromatic R in the approximate molar proportions of 2 mols of said hydrogen cyanide with 1 mol of said diisocyanate at a temperature less than 25° C. in the presence of a nonreactive solvent and a nitrogen containing cyclic ring compound catalyst which has no active hydrogens, has a basicity expressed in $K_b$ of no greater than $1 \times 10^{-8}$ and will not catalyze the reaction mixture to form polymers.

2. A process according to claim 1 wherein said catalyst is selected from the group consisting of pyridines having the formula:

and anilines having the formula:

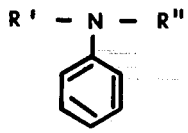

wherein R' and R'' are $C_1$–$C_{15}$, preferably $C_3$–$C_{10}$ and most preferably $C_3$–$C_6$ aliphatic groups for the pyridine, and preferably $C_2$–$C_{10}$ and most preferably $C_2$–$C_6$ aliphatic groups for the aniline.

3. A process according to claim 2 wherein the R' and R'' on said pyridine have from 3 to 10 carbon atoms.

4. A process according to claim 2 wherein the R' and R'' on said aniline have from 2 to 10 carbon atoms.

5. A process according to claim 2 wherein the R' and R'' on said pyridine have from 3 to 5 carbon atoms.

6. A process according to claim 2 wherein the R' and R'' on said aniline have from 2 to 5 carbon atoms.

7. A process according to claim 1 wherein said solvent is aromatic solvent.

8. A process according to claim 1 wherein said aromatic diisocyanate is diphenylmethanediisocyanate.

9. A process according to claim 1 wherein hydrogen cyanide and said catalyst are added in solution form to said aromatic diisocyanate.

10. A process according to claim 1 wherein said R has a molecular weight of 80 to 10,000.

11. A process according to claim 10 wherein said catalyst is selected from the group consisting of 2,6 dialkyl pyridines having the formula:

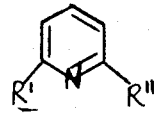

and N,N dialkyl anilines having the formula:

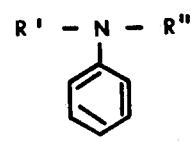

wherein R' and R'' are $C_1$–$C_{15}$, preferably $C_3$–$C_{10}$ and most preferably $C_3$–$C_6$ alkyl groups for the pyridine, and preferably $C_2$–$C_{10}$ and most preferably $C_2$–$C_6$ alkyl groups for the aniline.

12. A process according to claim 11 wherein said catalyst is the 2,6 dialkyl pyridine.

13. A process according to claim 11 wherein said catalyst is a N,N dialkyl aniline.

14. A process according to claim 11 wherein the R' and R'' on said pyridine has from 3 to 10 carbon atoms.

15. A process according to claim 11 wherein the R' and R'' on said aniline have from 2 to 10 carbon atoms.

16. A process according to claim 11 wherein the R' and R'' on said pyridine have from 3 to 6 carbon atoms.

17. A process according to claim 11 wherein the R' and R'' on said aniline have from 2 to 6 carbon atoms.

18. A process according to claim 11 wherein said solvent is aromatic solvent.

19. A process according to claim 11 wherein said aromatic diisocyanate is diphenyl methane diisocyanate.

20. A process according to claim 11 wherein hydrogen cyanide and said catalyst are added in solution form to said aromatic diisocyanate.

* * * * *